United States Patent [19]
Mortimore et al.

[11] Patent Number: 5,950,207
[45] Date of Patent: *Sep. 7, 1999

[54] COMPUTER BASED MULTIMEDIA MEDICAL DATABASE MANAGEMENT SYSTEM AND USER INTERFACE

[75] Inventors: William C. Mortimore, Muskego; Dwight A. Simon, Dousman, both of Wis.; Michael J. Gray, Novato, Calif.

[73] Assignee: Merge Technologies Inc., Milwaukee, Ill.

[ * ] Notice: This patent is subject to a terminal disclaimer.

[21] Appl. No.: 08/908,901

[22] Filed: Aug. 8, 1997

Related U.S. Application Data

[63] Continuation of application No. 08/384,943, Feb. 7, 1995, Pat. No. 5,740,428.

[51] Int. Cl.⁶ .................................................. G06F 17/30
[52] U.S. Cl. ............................................ 707/104; 707/100
[58] Field of Search ............................ 707/104, 100

[56] References Cited

U.S. PATENT DOCUMENTS

| | | | |
|---|---|---|---|
| 4,656,579 | 4/1987 | Bachman et al. | 364/200 |
| 4,994,987 | 2/1991 | Balwin | 364/518 |
| 5,019,975 | 5/1991 | Mukai | 364/413.13 |
| 5,085,185 | 2/1992 | Morris et al. | 123/193.6 |
| 5,229,585 | 7/1993 | Lemberger et al. | 235/375 |
| 5,241,472 | 8/1993 | Gur et al. | 364/413.22 |
| 5,258,855 | 11/1993 | Lech et al. | 358/462 |
| 5,264,684 | 11/1993 | Weil | 235/375 |
| 5,272,543 | 12/1993 | Yanagisawa | 358/403 |
| 5,321,520 | 6/1994 | Inga et al. | 358/403 |
| 5,359,702 | 10/1994 | Mukai | 395/109 |
| 5,369,508 | 11/1994 | Lech et al. | 358/462 |
| 5,384,643 | 1/1995 | Inga et al. | 308/403 |
| 5,416,602 | 5/1995 | Inga et al. | 358/403 |
| 5,418,355 | 5/1995 | Weil | 235/375 |
| 5,448,375 | 9/1995 | Cooper et al. | 358/375 |
| 5,486,686 | 1/1996 | Zdybel et al. | 235/375 |
| 5,544,284 | 8/1996 | Alleback et al. | 395/131 |
| 5,592,374 | 1/1997 | Fellegara et al. | 395/203 |
| 5,740,428 | 4/1998 | Mortimore et al. | 707/104 |

*Primary Examiner*—Paul V. Kulik
*Assistant Examiner*—Jean M. Corrielus
*Attorney, Agent, or Firm*—Michael A. Lechter; James H. Phillips; Squire, Sanders & Dempsey L.L.P.

[57] ABSTRACT

A computer database for medical imaging stores and manipulates multimedia data from various sources and reduces misidentification of data. A unique identifier is generated and linked to each data object, preferably at the time the image is generated. A graphical representation of the identifier is incorporated into the image or text when displayed or printed. A detector may be used to read the representation, allowing the identifier to be read and identify the data.

74 Claims, 7 Drawing Sheets

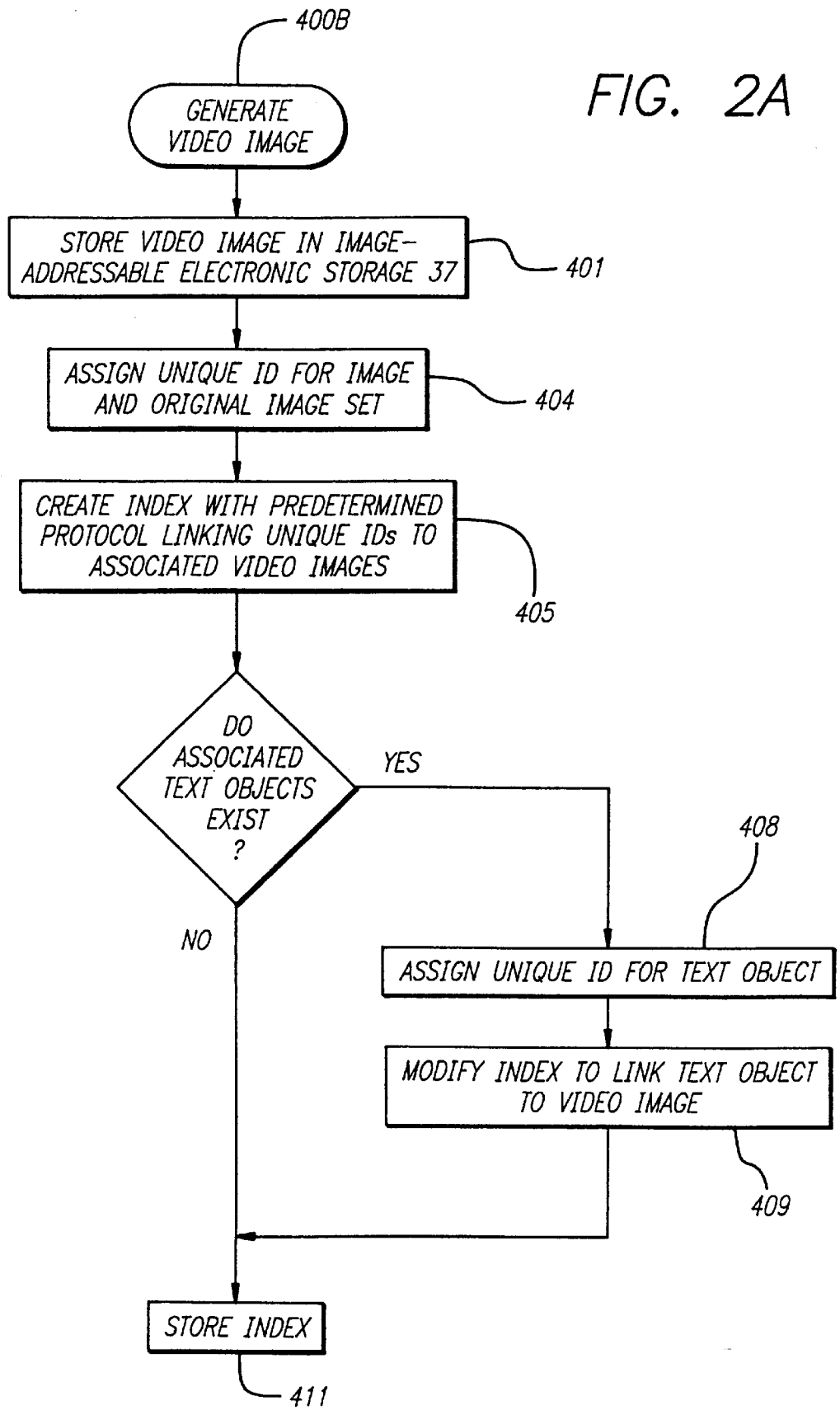

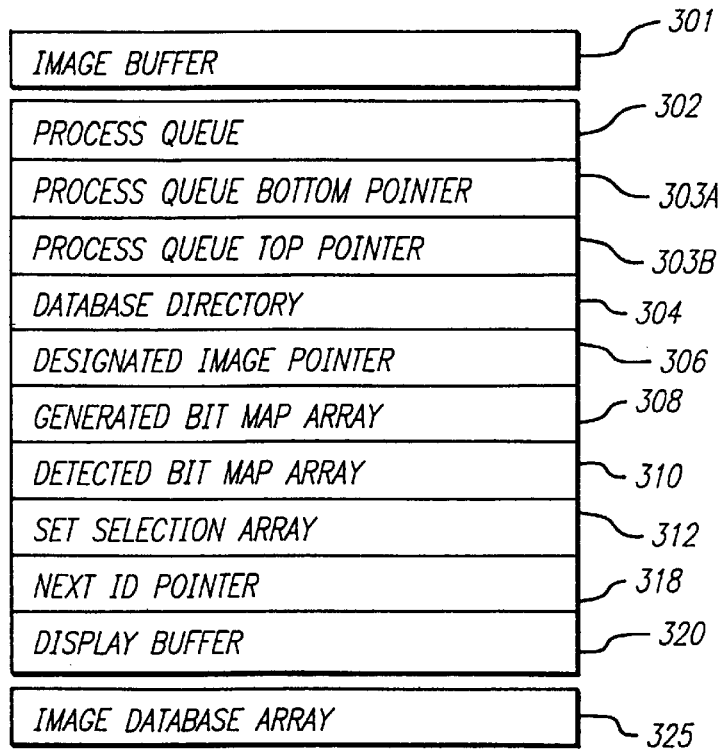
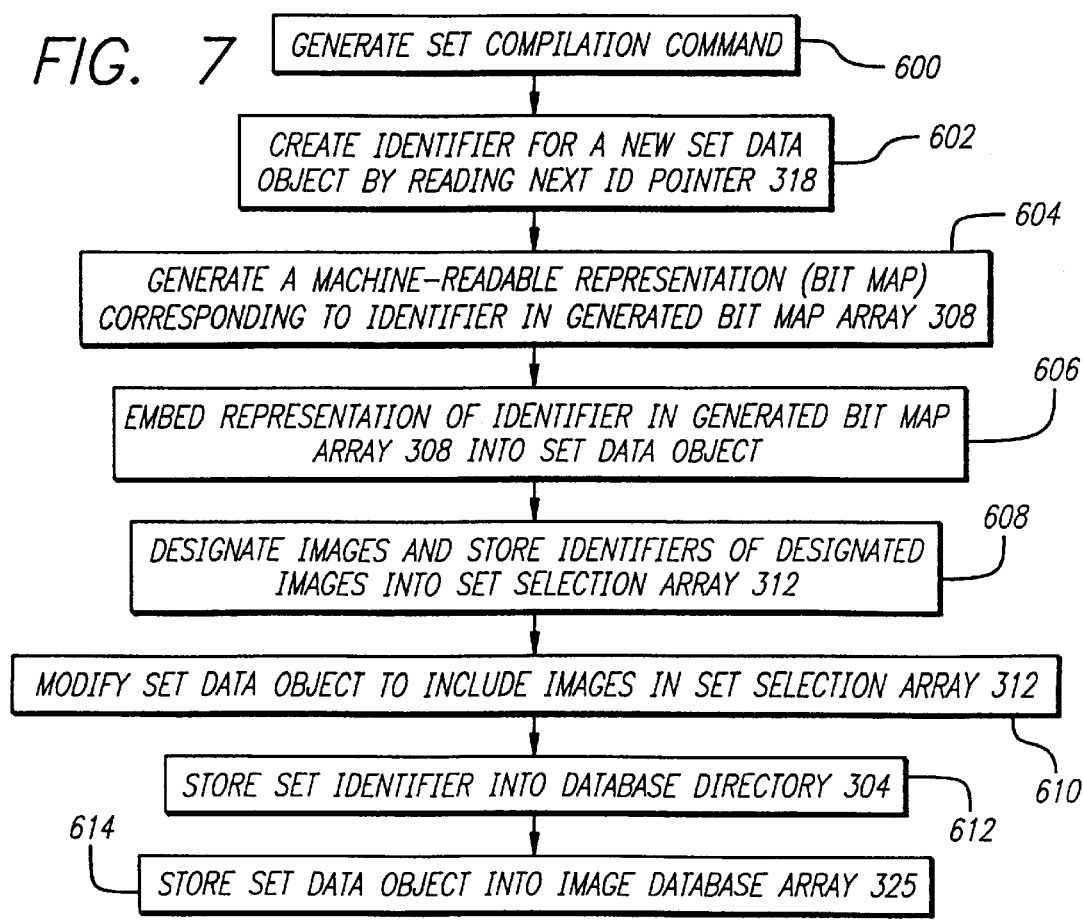

COMPUTER BASED MULTIMEDIA MEDICAL DATABASE MANAGEMENT SYSTEM AND USER INTERFACE

This is a continuation of U.S. Ser. No. 08/384,943 filed on Feb. 7, 1995 U.S. Pat. No. 5,740,428.

BACKGROUND OF THE INVENTION

1. Field of the Invention

Aspects of the present invention relate to management of multimedia information. More particularly, various aspects of the present invention relate to management systems for databases of multimedia medical data and related user interfaces.

2. Description of the Related Art

Despite the proliferation of computers, many medical doctors, particularly radiologists, prefer to analyze image data using hard copies, e.g., images on transparency film, reflective paper, or text printed on paper, instead of "soft copies" on an electronic display. Practitioners cite a number of reasons for this preference. For example, conventional electronic displays, such as cathode ray tubes ("CRTs"), cannot economically match the resolution of, for example, a sheet of film. Hard copies provide excellent contrast and resolution, and are accepted by radiologists. In addition, a radiologist often prefers to simultaneously view several full resolution images. Typically, the radiologist places multiple hard copies on a large light box. In contrast, typical electronic displays cannot provide such simultaneous viewing of multiple images without sacrificing resolution.

Hard copy systems, however, present a number of problems. Frequently, only a single set of hard copies is available. Accordingly, only one person can use a particular hard copy at any given time. A number of individuals, however, are commonly involved in a particular case, including the radiologist, treating physician or surgeon, and various other point of care professionals. As a practical matter, only the reading radiologist has ready access to the actual images. The remaining individuals receive the radiologist's written summaries instead of the actual images.

In addition, storing and retrieving hard copy images is inefficient and prone to errors. For example, film images must be labelled with the pertinent information, such as patient name, doctor, date, etc., which requires considerable time. In addition, the labelling process may introduce errors because the information must be typed or entered into a computer by hand. Even if the labels contain accurate information, they may be placed on the wrong hard copies, causing misidentification.

After labeling, the hard copies are generally placed in large file folders in a storage facility. Handling the large hard copies is cumbersome and difficult, and the size of the hard copies requires substantial storage space. In addition, if the hard copies are misfiled, retrieval becomes extremely difficult and time-consuming, if not impossible. Indeed, misfiling may cause virtual loss of the hard copies, for they can seldom be located after misfiling.

Hard copy analysis and archiving systems are often employed even where the original data is in digital form. Medical facilities often generate and maintain medical images, patient information, and diagnostic reports in a digital format, but present the information to the user as hard copies. Similarly, images generated by digital imaging techniques, such as ultrasound, nuclear medicine, digital fluorography or angiography, computerized tomography ("CT"), magnetic resonance ("MR"), and computerized radiography, are initially generated in digital form, then transferred to a hard copy for presentation to the radiologist or clinician. The hard copy is easier than the digital data for the analyst to access, handle, and visualize. The digital data, on the other hand, is often discarded immediately or shortly after creation; alternatively, the original digital data may be maintained only as a backup to replace lost or damaged hard copies, while the hard copies are traditionally used for analysis and long-term archiving.

It has been generally suggested that computer-based systems may replace hard copies with electronic displays and digital optical storage media. In these systems, multimedia data, such as digital image data and reports, are acquired through data acquisition interfaces and stored on electronic or computer media such as, for example, magnetic or optical disc drives. Banks of high resolution electronic displays present the image data to the radiologist, who makes a diagnosis from the visual presentation. High resolution displays, however, are costly, and many practitioners resist the transition from traditional hard copy systems.

In sum, the need for a comprehensive system for managing multimedia data remains unfulfilled. In addition, a user interface for a database management system that reduces errors caused by manual entry would be advantageous.

SUMMARY OF THE INVENTION

According to various aspects of the present invention, a computer database system for managing multimedia medical images, e.g. both hard copy (paper and film) and electronically stored images and data, automatically assigns a unique identifier to each data object. The system may further assign an identifier to groups of associated data objects. The identifier is preferably assigned when the data object is generated, and may be encoded into a machine-readable representation which is suitably printed on all hard copies of the associated image. With an appropriate reading device, a user may scan the representation which uniquely identifies the associated data object within the database.

Using the detector, human errors caused by manual entry of the identifier may be avoided. By permanently linking the data object to an associated unique identifier, the database stores the data object in electronic form and recalls the associated image or data at any time for printing in hard copy form, electronic transmission to another user or system, or compilation of a number of different data objects into a group having a separate and unique identifier.

BRIEF DESCRIPTION OF THE DRAWING

A preferred exemplary embodiment of the present invention is described in conjunction with the drawing, in which like designations denote like elements, and:

FIG. 2A is a flow diagram of a method of generating a unique identifier for an analog or digital data object in a database and for permanently linking the identifier to the data object set;

FIG. 3 is a representation of various sections of a memory for the server of FIG. 1;

FIG. 7 is a flow diagram of a method of compiling a group of data objects into a new group.

DETAILED DESCRIPTION OF A PREFERRED EXEMPLARY EMBODIMENT

Figure 1:
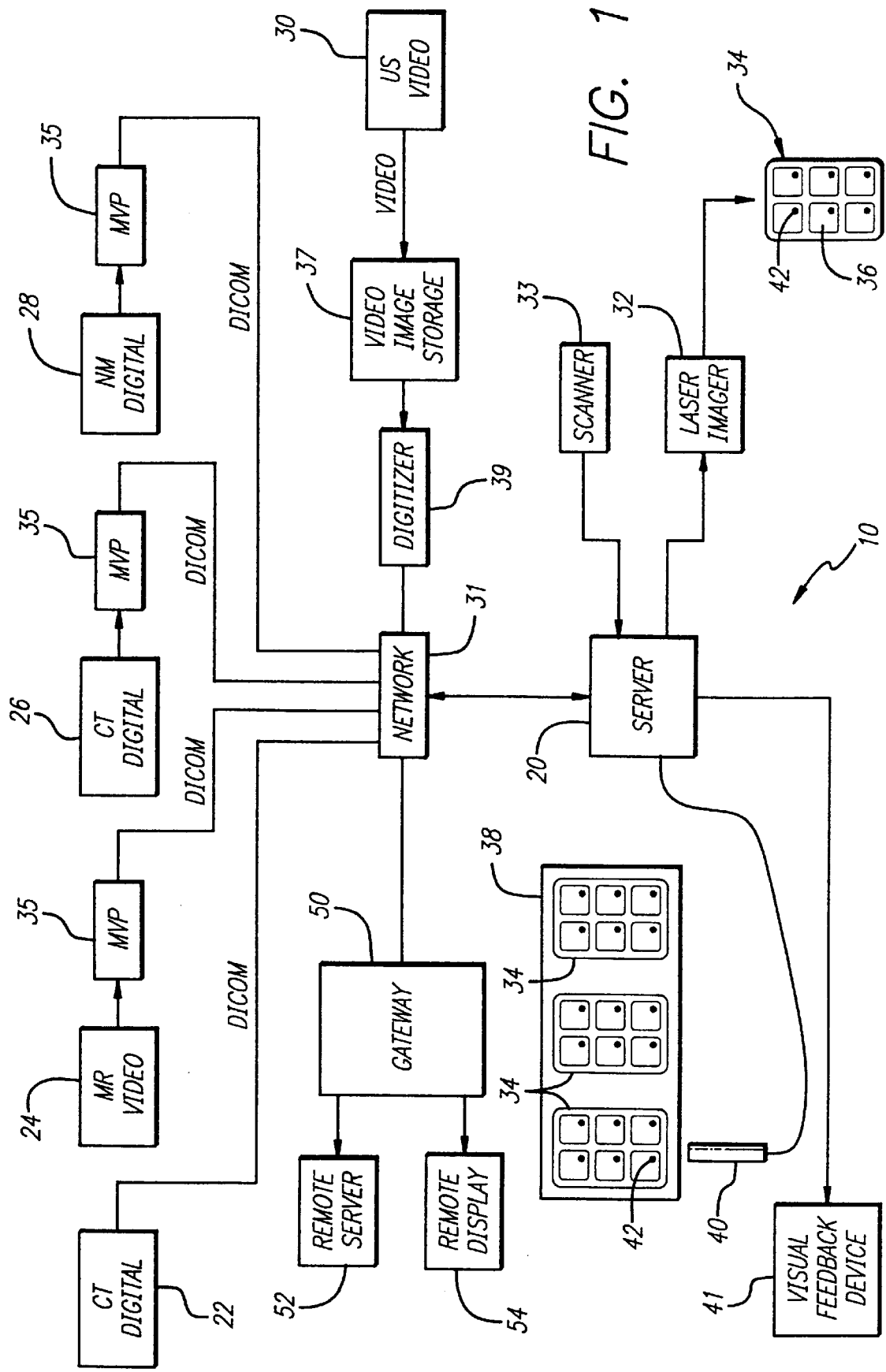
FIG. 1 is a block diagram showing various aspects of a computer based multimedia database management system in accordance with certain aspects of the present invention.

Referring to FIG. 1, a database management system 10 according to various aspects of the present invention for multimedia medical data, such as X-rays, CT scans, MR scans, textual data, and the like, suitably comprises: a server 20; one or more data sources, including respective computerized tomography (CT) imaging devices 22 and 26, a nuclear medicine (NM) imaging device 28, a magnetic resonance (MR) imaging device 24, an ultrasound (US) imaging device 30, and a scanner 33; a suitable communication network 31; one or more conventional hard copy peripherals, such as a conventional laser imager 32; a suitable detector 40; and a visual feedback device 41. The functions described as being attributed to a particular component of system 10, however, may be distributed throughout system 10. Laser imager 32, scanner 33, detector probe 40, visual feedback device 41, and various other devices may be coupled directly to server 20, or may be coupled to server 20 via network 31.

Data sources may include any device for generating data, such as devices which generate output suitable for electronic storage. For example, respective computerized tomography (CT) imaging devices 22 and 26 and nuclear medicine (NM) imaging device 28 typically generate digital data; magnetic resonance (MR) imaging device 24 and ultrasound (US) imaging device 30, on the other hand, typically generate video signals. Other sources of data in system 10 may include text data sources, such as a keyboard or a voice recognition input system (suitably a part of or associated with server 20, one or more of the imaging devices, or both). Scanner 33 also suitably provides digital data corresponding to scanned images and text, such as radiology films, reports, lab results, clinical notes, and the like.

Preferably, each data source generates data in a predetermined standard file structure which coherently and uniquely identifies each data object, e.g. image, data set, or group of images and data sets, regardless of source. Each data source suitably generates an identifier, suitable for storage in the database, in accordance with the file structure. For example, CT imaging device 22 may generate image data in a suitable standard file structure such as DICOM v3.0, described in greater detail below, which provides a standard for generating unique identifiers associated with each image and data set.

If a data source does not generate the data in an appropriate format, the output may be converted to, accommodated by, or referenced by the selected standard file structure. For example, a data source may generate an output in another format, such as a different digital format or an analog format. In that case, the output may be digitized, if necessary, and converted to the appropriate file structure by a suitable external interface device 35, such as a commercially available Merge Technologies Merge MVP™ interface.

Various data sources, such as ultrasound (US) device 30, may create images in video (i.e. non-digital) or similar formats. Such data may be temporarily stored in a suitable memory until the data is to be digitized and formatted according to the standard file structure. For example, the images generated by US device 30 may be provided to a video image storage system 37. Video image storage system 37 suitably comprises a video disk or video tape system for recording the video images generated by US device 30 until the images are accessed by server 20. Images retrieved from video image storage system 37 may be digitized by a digitizer 39, converted to the standard file structure by server 20, and stored and modified by server 20 as they are needed.

The data generated by data sources 24, 26, and 28 is shown passing through respective external interface devices 35 to put the data in an appropriate file structure. Alternatively, the non-digital data from MR data source 24 may be digitized by a digitizer (not shown), and the digital data from data sources 24, 26, 28 and 30 (after digitization by digitizer 39) may be converted to an appropriate file structure by server 20.

Data may also be generated directly from hard copies using scanner 33 to provide electronic data representative of the corresponding images and text. Scanned data may then, if necessary, be converted to the appropriate format and assigned a unique identifier as required by the database by either scanner 33 or server 20. Data with an embedded identifier may also be read from film or paper using scanner 33, with the resultant data and unique identifier being compiled into the format required by the database.

In each of the cases described above, the data is permanently linked to a unique identifier. For example, the identifier may be appended to the data and, in effect, embedded in the data itself. The various data sources may also include input mechanisms, e.g., keyboards, for entering appropriate information which is encoded in the identifier. Identifiers are preferably universally unique to each individual image or text object created by the data sources.

One example of a scheme for generating and assigning a universally unique identifier is described in relation to the DICOM v3.0 file format. Each unique identifier is composed of a "root" and a "suffix." In an example presented in Annex B to DICOM—Part 5: Data Structures and Encoding (NEMA Standards Publication No. PS 3.5-1993), a unique identifier of 1.2.840.xxxxx.3.152.235.2.12.187636473 is presented. The root is "1.2.840.xxxxx," while the remaining portion is the suffix. Each field is suitably separated by a period. The first digit of the root is "1", which signifies the International Standards Organization (ISO), and the second digit of the root is "2", which signifies an ANSI member body. The next three digits provide a country code of a specific ANSI member body, with the "840" corresponding to the United States. Next, five more digits, represented by "xxxxx", identify a specific organization registered with ANSI. In this manner, each organization registered with ANSI has a unique root.

It should be noted that ISO and ANSI occasionally change the technique for deriving a root. For example, a more current root has been issued by ANSI other than the one identified in the example above, specified as 2.16.840.xxxxxx. Regardless of its specific format, however, the root acts as a unique identifier for each company and organization registered with ISO and ANSI.

The fields in the suffix in the above example illustrate a method for an organization to assure the uniqueness of its identifiers. The first digit ("3" in the example) in the suffix defines the device type, and the next three digits ("152") contain the device serial number. Three more digits ("235")

identify the study number, followed by another digit ("2") to identify the series number, and two more digits ("12") to identify the image number within this particular study and series. Finally, the last nine digits ("187636473") comprise an encoded date and time stamp of image acquisition. The respective identifier fields, when concatenated, uniquely identify original sets of image objects and each individual image within the set.

Figure 2:
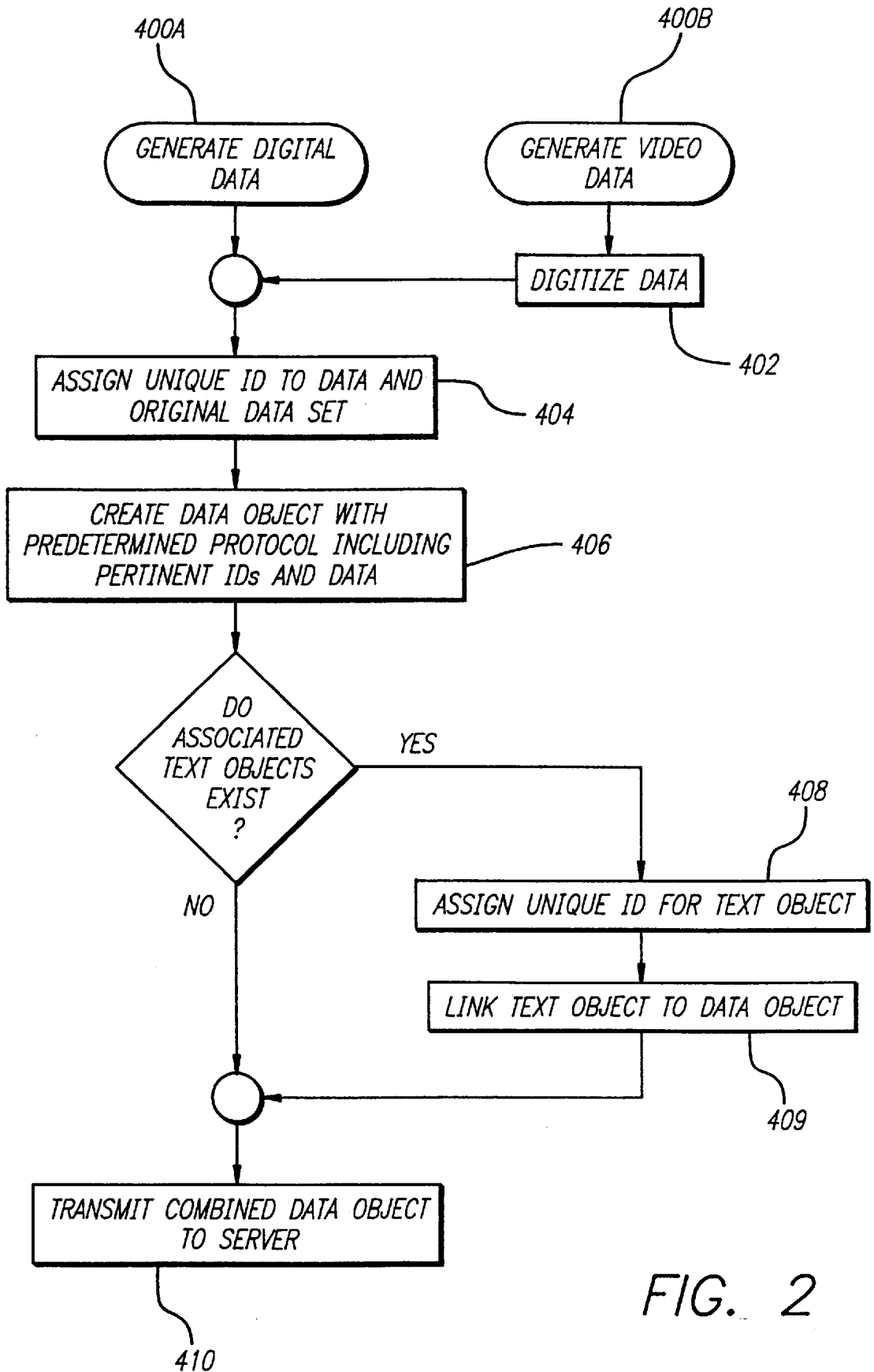
FIG. 2 is a flow diagram of a method of generating a unique identifier for a data object in a database and for permanently linking the identifier to the data object.

Preferably, the data source generates and assigns the identifier in accordance with the standard file structure. As described above, the identifier suitably comprises 64 digits or less, and may accommodate pertinent information relating to the data (such as a patient name, radiologist, treating physician, time and date, etc.). For example, referring now to FIG. 2, one of the data sources may generate data, such as digital or video data (steps 400A, 400B). If the data is not in digital form, e.g., a video signal, it is suitably digitized (step 402), for example by digitizer 39. A unique identifier may be assigned to the data, and preferably to each original data set, e.g., images corresponding to slices from the same CT scan (step 404). The data and its corresponding identifier are suitably assembled as a data object in accordance with the predetermined format or protocol (step 406) by formatting the data and identifier in accordance with the selected file structure. For example, this function may be performed by digital data sources, such as CT digital device 22, and by Merge MVP interfaces 35 coupled to data sources 24, 26 and 28 by formatting the digital data into a DICOM v.3.0 file containing unique identifiers for each data object. Thus, assigning identifiers at the source of the data assures that all data receives an identifier.

Text objects may also accompany the image data. Any text objects (e.g. patient name, date, reports, etc.) related to an image or set of images created at any point in the process (whether at the imaging device or otherwise) may be linked with the data by assigning an identifier (step 408) to the text object. Text objects may include, for example, information regarding the images or the patient, or other notes and comments from hospital staff. The text object and data object may then be linked (step 409), for example according to their respective identifiers. For example, a separate identifier may be assigned to a data object containing the identifiers for both the text object and the data object, as well as any other associated data. This separate identifier is then encoded into all hard copies of any of the objects. As a result, reference to the identifier of any object in the set links the particular data object to all of the related objects. The data objects and associated text objects are suitably communicated to server 20 (step 410), e.g., through network 31, direct serial interfaces, magnetic tape, removable disk media, or other suitable mechanism.

For some non-digital systems, alternative methods of storing the data and assigning identifiers may be suitable. For example, referring to FIG. 2A, a supplementary method of creating unique identifiers may be employed for a non-digital imaging system, such as US device 30 (FIG. 1). Video images from US device 30 are initially generated (step 400B) and suitably stored in an image-addressable electronic storage, such as video image storage 37 of FIG. 1 (step 401). Data stored in video image storage system 37 may be stored in accordance with an independent file structure. Server 20 may generate a unique identifier and assign an identifier to each video image, and suitably to each original image set, e.g., images from the same US scan (step 404). Server 20 also suitably creates an index for linking the address of each image in video image storage 37 to the associated unique identifier (step 405).

If a text object is associated with a video image, a unique identifier is assigned to the text object (step 408), and the index is suitably modified to link the text object to the proper video image or set of images (step 409). The index may then be stored by server 20 (step 411), while the actual video data remains stored in video image storage 37 until accessed by server 20. With this system, each image stored in video image storage 37 may be uniquely identified by its corresponding identifier in the index. The generation and assignment of the identifier, creation of the index, and association of the text objects are preferably performed by server 20, though such tasks may also be performed by other system 10 components, such as US device 30, or an external interface device coupled between digitizer 39 and network 31 (not shown).

Data generated by data sources and the corresponding identifiers may be provided to server 20, suitably through network 31, for storage, transmission, and transformation into hard copies. Network 31 may include any suitable communications network, such as a 10-base T local area network (LAN) employing twisted pair cables. In addition to server 20, network 31 may also communicate with a remote server 52 or remote display device 54, either of which may be integrated into the network or connected to the network through a suitable gateway 50. Network 31 may incorporate any form of communications media, including dedicated wire connections (as shown in FIG. 1), modem connections over telephone lines or dedicated cables, infrared or RF transmitter/receiver, microwave transmitter/receiver, satellite communications, transportable magnetic tape, floppy disk, etc.

Server 20 suitably comprises a conventional computer having high throughput to service multiple peripherals. Server 20 is suitably connected to network 31 for receiving and transmitting data to and from the various data sources, peripherals, and remote stations. In addition, server 20 preferably includes a memory having sufficient storage capacity to store data for a large number of images and other data objects as required by the particular system. Server 20 may further comprise a central bus suitably coupled to a variety of peripheral devices (e.g. disk drives, display monitor driver, networking hardware, etc.).

In particular, referring to FIG. 3, the memory of server 20 suitably comprises: an image buffer 301; a process queue 302, a process queue bottom pointer 303A, and a process queue top pointer 303B; a database directory 304; a designated image pointer 306; a generated bit map array 308; a detected bit map array 310; a set selection array 312; a next identifier pointer 318; a display buffer 320; and an image database array 325. It should be noted that FIG. 3 illustrates only the various names for designated portions of the memory. FIG. 3 does not represent a memory map of the present system, but simply lists various items included in the memory system.

Data received by server 20, for example from one of data sources 22, 24, 26, 28, and 30, may be initially received by image buffer 301. To accommodate rapid transmission of data, image buffer 301 suitably comprises a shift register. Data accumulated in image buffer 301 may then be transferred to process queue 302. Process queue 302 suitably comprises a series of contiguous memory locations, such as in RAM, and preferably at least equal in number to the maximum number of data objects in an original set, e.g. images in a scan plus attendant text objects. Process queue 302 is suitably organized as a first in, first out (FIFO) queue for storing incoming data prior to processing.

Process queue top and bottom pointers 303A and 303B are suitably memory locations that point to the top and bottom locations available within process queue 302. Queue bottom pointer 303A indicates the next memory location available for data received from image buffer 301. As data objects enter process queue 302, queue bottom pointer 303A is adjusted (e.g. incremented or decremented by the number of bytes in the data object) to advance to the next available location in process queue 302. Queue top pointer 303B, on the other hand, suitably points to the location of the oldest data in process queue 302. Thus, queue top pointer 303B indicates the next data in process queue 302 to be processed.

Data in process queue 302 at the location indicated by queue top pointer 303B may be forwarded to display buffer 320. Display buffer 320 suitably comprises an array of contiguous memory locations containing display data received from process queue 302. Server 20 suitably extracts the identifier associated with the data in display buffer 320 from the data object, encodes the identifier according to a predetermined algorithm (as described further below), and converts the result into pixel values which constitute indicia or a representation of the identifier. The representation suitably comprises a three-dimensional array (X, Y, Z, where X and Y are spatial coordinates and Z is, e.g., a gray scale value). The encoding algorithm preferably generates a machine readable representation that is readable by a reading device (e.g. detector 40) regardless of the orientation between the representation and the reading device. In addition, the encoding algorithm suitably provides sufficient resolution for error checking and for encoding all of the information in the identifier.

An exemplary algorithm for encoding the identifier is the embedded data glyph developed by Xerox, described in *Embedded Data Glyph Technology for Hardcopy Digital Documents*, Society of Photo-optic Instrumentation Engineers Vol. 2171 Color Hardcopy and Graphic Arts III (1994), by David L. Hecht. The varying gray scales of the Xerox glyph produce a gray scale identifier representation on the hard copy which does not distract the user when the hard copy film is placed on a light box for viewing. The use of gray scales allows a large amount of information to be encoded in a small space. Other machine readable formats, however, such as bar codes, may also be used.

If server 20 determines that no identifier has yet been assigned to the data in display buffer 320, server 20 preferably assigns a unique identifier. For example, server 20 may access next identifier pointer 318 to obtain an appropriate identifier. Next identifier pointer 318 suitably comprises a register containing an unused identifier (suitably comprising a root and suffix as described above) for an image or set of images created by server 20, such as by compiling one or more images in image buffer 301 into a new set of images (as described further below), by server 20 reading a hard copy image using scanner 33, or by server 20 reading a digitized video image from digitizer 39.

Generated bit map array 308 stores the converted pixel values for the identifier. Generated bit map array 308 suitably includes an array of contiguous memory locations, such as in RAM. Data in display buffer 320 is suitably modified to integrate the representation of the identifier in generated bit map array 308 into the data in display buffer 320.

After modification to integrate the identifier representation, data in display buffer 320 is suitably transferred to image database array 325. Image database array 325 stores not only images, but text and other relevant information as well. Image database array 325 suitably comprises the main memory for data generated, maintained, and accessible by the system. Because of the extremely large number of data objects likely to be stored in the system, image database array 325 suitably includes a mass storage system, such as a tape drive, optical drive, or hard drive array.

The identifier for each image stored in image database array 325 and video image storage 37 is stored in database directory 304. Database directory 304 suitably comprises a series of contiguous memory locations, also suitably in mass storage such as a hard drive array, preferably at least equal in number to the maximum number of images to be stored in image database array 325 and video image storage 37. Database directory 304 preferably contains one identifier for each image and set of images stored.

Detected bit map array 310 suitably receives data from detector 40. Detected bit map array 310 suitably comprises an array of contiguous memory locations of similar size and configuration as generated bit map array 308. As described in detail below, detector 40 suitably detects the representation of the identifier associated with a data object embedded in a hard copy. The digital signal from detector 40 suitably accumulates in bit-mapped three-dimensional detected bit map array 310. Detected bit map array 310 stores the pixel data for decoding by server 20 to generate the identifier associated with the data, thus enabling server 20 to selectively retrieve data from image database array 325 or video image storage 37.

Set selection array 312, comprising, for example, an array of contiguous memory locations, suitably stores the identifiers of images designated by a user to be compiled into a set. For example, a radiologist may designate several specific images using detector 40 to select the individual identifiers. The relevant identifiers may be maintained in set selection array 312 until the radiologist completes his selections. Upon completion, server 20 suitably reads the identifiers from set selection array 312 and assembles them into a set, as described in greater detail below.

Finally, designated image pointer 306 suitably comprises a register containing the memory location of an image in image database array 325 or in video image storage 37 to be transmitted to a remote device. For example, an operator (remote or local) may select an image to be transmitted using the corresponding identifier. Server 20 suitably loads the selected unique identifier from database directory 304 and writes a value corresponding to the appropriate memory location to designated image pointer 306. Server 20 retrieves the designated data object from the location in image database array 325 or video image storage 37 pointed to by designated image pointer 306, and transmits the selected image to the operator's station.

As discussed above, server 20 preferably receives the data in a standard format. If the data is in digital form, server 20 suitably modifies the data object to, in effect, unobtrusively embed a machine readable representation of the identifier into the data object. If the data object is in video or other non-digitized format, server 20 may link an index of unique identifiers to the addresses of the non-digital images, and suitably store the index with database directory 304. In either case, a unique identifier is suitably linked to each data object. If a hard copy is generated from the database, the hard copy suitably contains the unique identifier in graphical, machine-readable format, regardless of whether the stored image is in digital or video form.

Figure 4:
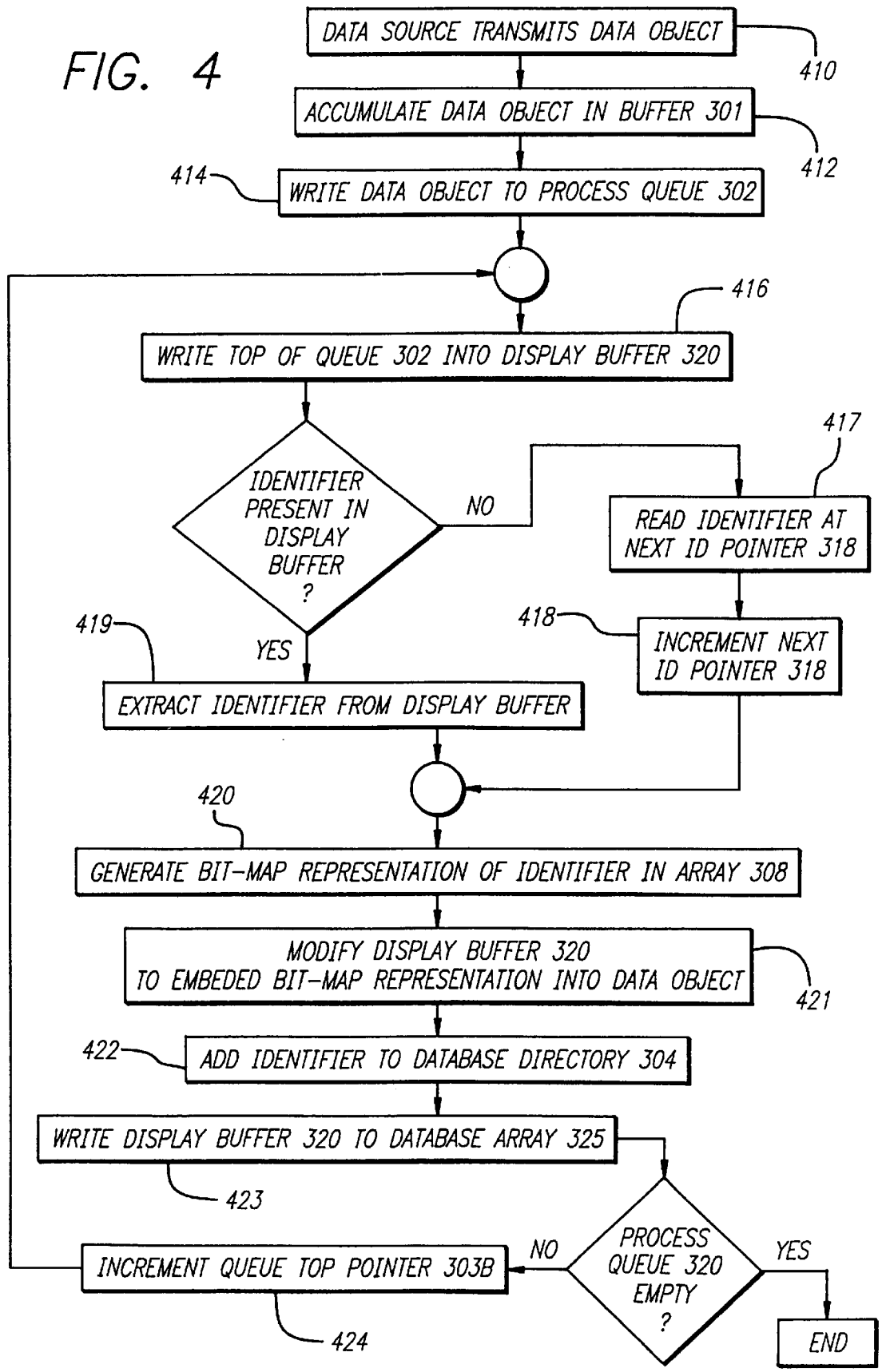
FIG. 4 is a flow diagram of a method for embedding an identifier into a data object.

Referring to FIG. 4, after a data object is generated by a data source, converted to the appropriate format, and preferably assigned an identifier, the data object may be transmitted, suitably through network 31, to server 20 (step 410). The data suitably accumulates in image buffer 301 (step 412), and may then be written into process queue 302 at a location designated by queue bottom pointer 303A (step 414).

The data object at the top of process queue 302 (i.e. designated by queue top pointer 303B) is then suitably loaded into display buffer 320 (step 416). As discussed previously, if no identifier has been assigned, server 20 may read a suitable identifier from next identifier pointer 318 (step 417). Next identifier pointer 318 is then suitably adjusted, e.g. incremented, to provide the next available identifier (step 418). If the data object has an identifier embedded therein, the identifier is suitably extracted from the data object (step 419). The identifier, whether extracted from the data object or generated by server 20, may then be encoded in accordance with a suitable predetermined algorithm, and a machine-readable representation of the identifier may be generated (step 420).

The data object in display buffer 320 may then be modified to effectively embed the bit-mapped representation of the identifier in an unobtrusive area of the data object, e.g., the lower right hand corner of an image (step 421). For example, the gray scale values of the bit mapped representation may be added from generated bit map array 308 to the data object, effectively on a pixel by pixel basis, beginning at a predetermined relative address within the data object in display buffer 320.

The identifier may be written into database directory 304 (step 422), and the modified image data (the "tagged data object") is suitably written to image database array 325. If more data objects remain in process queue 302, queue top pointer 303B may be then adjusted to advance the process to the next data object in process queue 302 (step 424), and the next data is retrieved from process queue 302.

By integrating representation 42 into the hard copy, each image 36 and set of related images is uniquely identified, and has the identification integrally embedded in the image itself. Embedding corresponding machine readable representation 42 into each image and each image set, in effect making the representation 42 an integral part of the image data, is particularly advantageous, for it serves to reduce many human errors, including mislabeling, misreading, and misentering identification numbers.

At the time the data is generated, the tagged data object may also be provided to a hard copy generating peripheral. Hard copy 34 (FIG. 1) suitably comprises, for example, a transparency, film, or paper print in accordance with the data object. The hard copy generating peripheral suitably comprises any device capable of generating a hard copy in a page format, e.g. conventional laser imager 32.

After the data has been generated and provided to server 20 for modification and integration into the database, the radiologist or other analyst may view the complete set of data, for example images, on video monitors. In addition, the analyst may view a hard copy 34 of the images on translucent sheet(s) of film, such as a typical sheet of x-ray film. Referring again to FIG. 1, hard copy 34 is typically viewed on a light box 38. Several hard copies 34 may be viewed at one time, with each hard copy containing one or more images 36 with corresponding representations 42. In practice, the radiologist identifies and designates those images or sets of images that are relevant to a particular issue or to a particular point of care professional.

A particular image or set of images is designated by reading representation 42 associated with the image or set of images using detector 40 (FIG. 1) suitable for reading the particular representation incorporated into hard copy 34. For example, detector 40 may comprise any mechanism capable of detecting and generating a signal indicative of the bit map of the representation 42, such as a handheld detector probe. Detector 40 preferably utilizes visualization technology capable of "imaging" representation 42, i.e. generating a series of digital signals corresponding to the respective pixel values of representation 42. For example, detector 40 may, in effect, perform a raster scan of representation 42 to generate gray scale signals on a pixel by pixel basis.

The digital signal received by server 20 from detector 40 is suitably accumulated in bit-mapped three-dimensional (X,Y,Z) detected bit map array 310, representing a precise digital image of the original representation 42. The bit-mapped version of representation 42 is then suitably decoded employing the converse of the predetermined encoding algorithm to produce the original unique identifier. The identifier may be used, in conjunction with directory 304, to identify the locations in image database array 325 or video image storage 37 where the data object corresponding to the hard copy is stored, and for selectively retrieving information relating to the designated hard copy image or set of images. This allows the operator to access any data previously stored with respect to image 36 or related images, e.g. a treating physician wanting to examine images in addition to those provided by the radiologist.

A feedback device responsive to detector 40 may be included to verify successful scanning of representation 42. For example, detector 40 may emit an audible beep to indicate that representation 42 has been successfully read. Visual feedback device 41 (FIG. 1) may also be provided to verify that the image read by detector 40 is the desired image. Visual feedback device 41 suitably comprises an electronic display, such as a CRT, a liquid crystal display (LCD) panel, or other visual display allowing text or graphical information to be displayed. Visual feedback device 41 suitably displays verification information, such as the patient name, image number, and date, or all or a portion of the actual image, either alone or in combination with text.

System 10 may suitably be further configured to permit an operator to designate individual images to assemble sets, subsets, and supersets of images from original sets of hard copy images 36. For example, individual images 36 may be selected from several different hard copies 34, such as by using detector 40. The designated images may then be selectively transmitted to remote server 52 for display, as described in greater detail below, or to a hard copy generation device, such as laser imager 32, for review by a point of care professional.

Figures 5, 6:
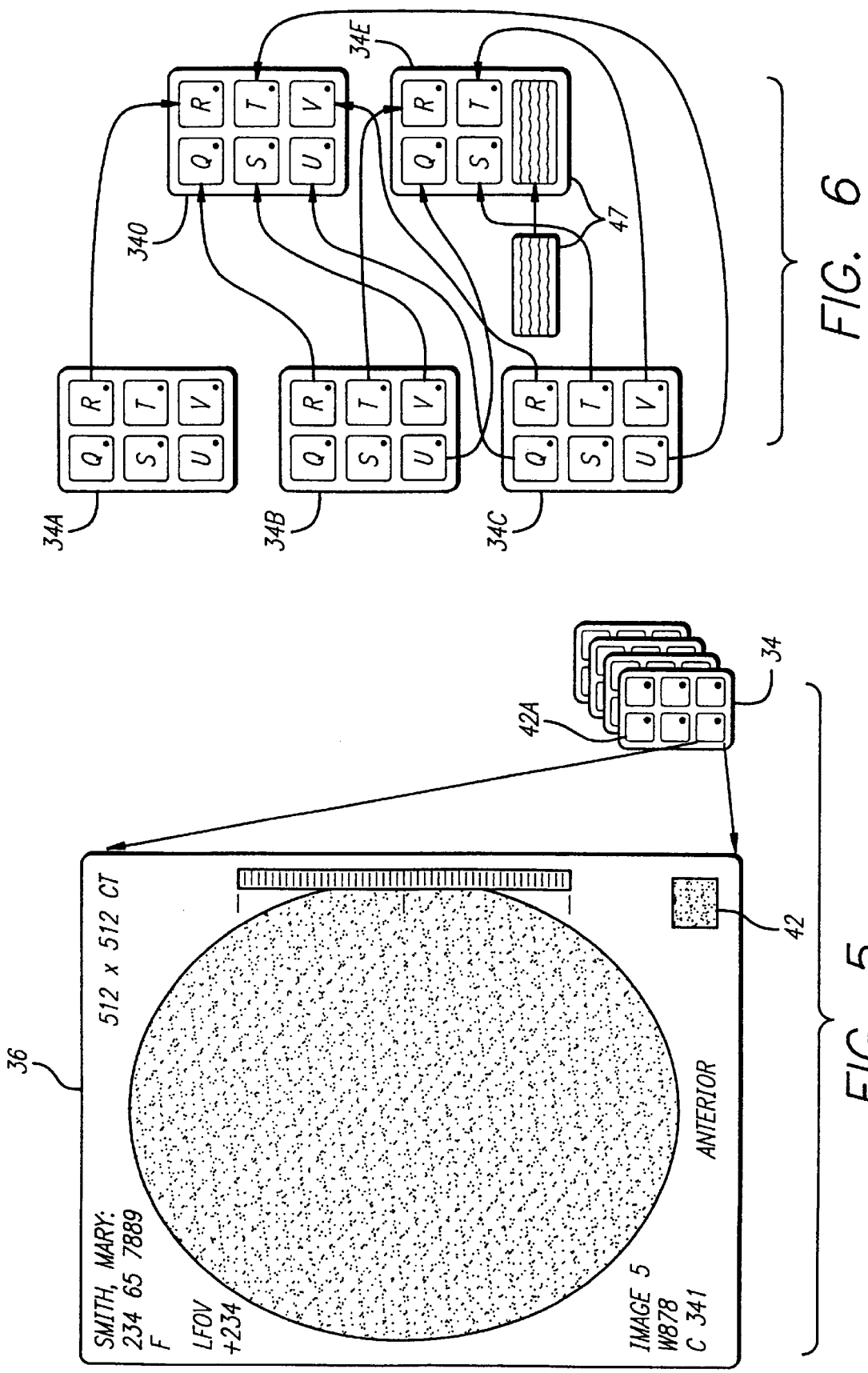
FIG. 5 is an enlarged view of a data object on a hard copy showing multiple image and text data objects and their corresponding identifiers.
FIG. 6 is a block diagram illustrating editing features of the exemplary database system of FIG. 1.

If desired, a machine readable representation corresponding to a set of images, e.g. all of the images associated with an original CT scan, may also be incorporated into the hard copy to facilitate identification of the set. A separate representation may also be provided for particular groups, subsets or supersets of related images on a hard copy sheet or plurality of sheets. For example, as illustrated in FIG. 5, server 20 may generate representation 42A associated with the set of images. Representation 42A is suitably embedded on an unused portion of hard copy sheet 34, e.g. in a border.

The decoded identifiers of the individual image and text objects designated in a discrete editing operation may be accumulated in a new file representing an edited examination or patient data subset. As described above, this edited data set may then be assigned a separate identifier which is added to database directory 304, and a corresponding representation may be generated and embedded in the member images to facilitate future access. Thus, hard copies 34 including only particular images of interest may be assembled, and only the most pertinent data may be selected for transmission to point of care professionals or for archiving. As a result, less relevant images or data from a larger collection may be eliminated to promote efficiency and reduce distraction and storage requirements.

This editing feature is further illustrated in FIG. 6. Three hard copy sheets 34A, 34B and 34C each suitably contain six images 36 with their corresponding representation 42 disposed at respective positions Q, R, S, T, U and V. Custom design of sets of images 34D may be assembled according to the analyst's specific parameters and needs by designating specific images, such as by using detector 40. Individual images from hard copy sheets 34A, 34B and 34C may be assembled on a single sheet, such as frame 34E of FIG. 3, along with related text 47 into one frame.

More specifically, referring to FIG. 7, an appropriate command (e.g. via keyboard) provided to server 20 suitably initiates the editing function (step 600). A unique identifier may be assigned to the new set data object from next identifier pointer 318 (step 602). The identifier may be encoded according to the predetermined bit-mapping algorithm to generate an array of gray scale values corresponding to a suitable unique machine readable representation of the set identifier in generated bit map array 308 (step 604). The representation is then embedded into a non-obtrusive portion (e.g. margin) of the set data object (step 606).

The particular images to form the set may be designated using detector 40, and the corresponding identifiers are suitably written into set selection array 312 (step 608). When the images are viewed in hard copy form, detector 40 may be employed to read embedded representation 42 in the images, and the identifiers may be derived according to the previously described decoding process. After all members of the set have been designated, the set data object is modified to include the images in set selection array 312 (step 610). The set identifier is then written to database directory 304 (step 612), and the resultant set data object is stored in image database array 325 (step 614). For example, the entire set of data may be collected into a single object, assigned an identifier, and provided with the appropriate encoded representation. Therefore, each time the set is designated for display, the machine readable representation associated with the set is generated on the hard copy sheet in a predetermined relationship to the images which is readily discernible to the user, e.g. in the margin next to each image, or on each sheet of hard copy representing the set.

Figure 8:
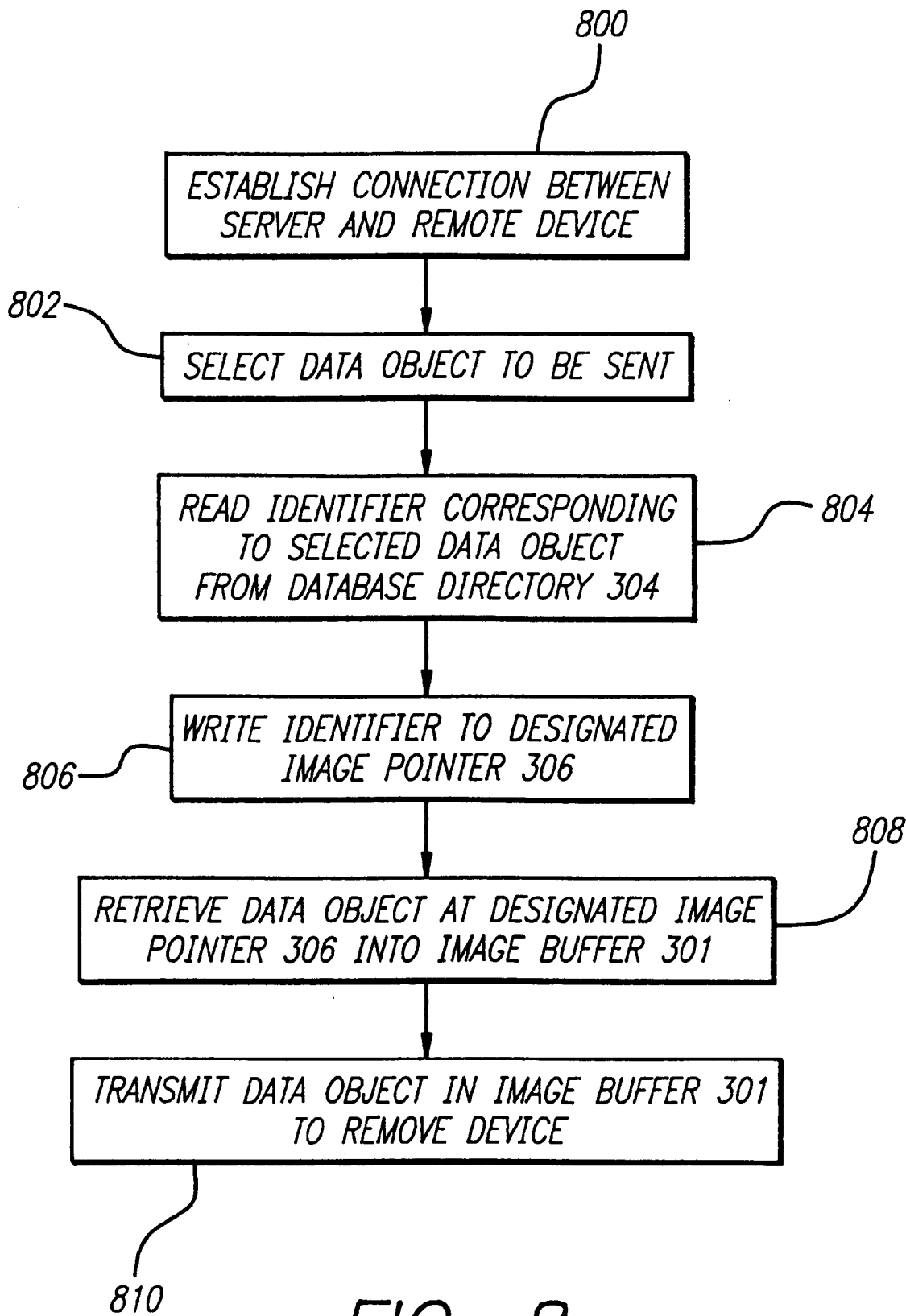
FIG. 8 is a flow diagram of a method for sending a data object to a remote device.

Referring again to FIG. 1, server 20 may further transmit designated data objects to remote servers (or other stations such as displays, hard copy generators, etc.) through network 31. As described above, network 31 suitably comprises a communications network such as a 10-base T local area network (LAN) employing twisted pair cables. Network 31 suitably communicates with a remote server 52 or remote display device 54. For example, referring to FIG. 8, data may be transmitted to a remote location by first establishing a connection between server 20 and a remote device, such as remote server 52 or remote display 54 (step 800). This connection may be initiated by either server 20 or the remote device 52, 54. The operator may then select which data object is to be transmitted (step 802) by providing the appropriate identifier or other suitable information. Server 20 then suitably reads the selected identifier from database directory 304 (step 804), and writes this value to designated image pointer 306 (step 806). Server 20 may retrieve the designated data object from the location in image database array 325 or video image storage 37 pointed to by designated image pointer 306, and store this data object in image buffer 301 (step 808). Server 20 then suitably transmits the selected data object in image buffer 301 to the remote device (step 810).

The ability to selectively designate images for transmission to points of care is particularly significant in view of the finite bandwidth and transmission speeds of network 31. In a fully interactive system, server 20 would also respond to commands from a remote server to send frames as required for viewing on an electronic viewing station or for printing only the selected images on a hard copy output device, such as laser imager 32. This configuration may permit an operator at a remote site with remote server 52 to examine the images stored in image database array 325 and in video image storage 37, and to edit the images in the same way as the local operator.

In sum, an information management system according to various aspects of the present invention advantageously stores, organizes, and reproduces multimedia data in a database. Although data is stored electronically, the data may be originally produced in any appropriate form, including digital, analog, film, or print. To manage and organize the data, each data object is assigned a universally unique identifier, and a representation of that identifier is automatically incorporated into each hard copy of the data to prevent misidentification. The representation tends to reduce entry errors common to typical manual entry systems.

In addition, the system suitably includes an advantageous editing feature, which permits medical personnel to designate particular data objects and collect them into a set. Consequently, only the most relevant data may be assembled into a set for analysis, storage, and transport. This feature is particularly advantageous for systems connected to an electronic transmission mechanism, such as a network or modem, for transmitting data to various locations within an organization. Instead of transmitting the enormous amount of information acquired in accordance with a procedure like a CT scan, only selected, particularly relevant images are transmitted. As a result, the transmission time and convenience to the operator is significantly improved.

The foregoing description of a preferred exemplary embodiment and best mode of the invention known to the applicant at the time of filing the application has been presented for the purposes of illustration and description. It is not intended to be exhaustive or to limit the invention to the precise form disclosed, and obviously many modifications and variations are possible in light of the present description. The various embodiments were chosen and described in order to best explain the principles of the invention and its practical application to enable others of ordinary skill in the art to best utilize the invention in various embodiments and with various modifications as are suited to the particular use contemplated.

We claim:

1. A method of managing multimedia medical data, wherein the data are visually presentable in hard copy form, comprising the steps of:

generating a data object representative of the medical data;

assigning a first unique identifier to the data object; and integrating a machine readable graphical representation of the first unique identifier into substantially all hard copies of the corresponding medical data represented by the data object.

2. The method of claim 1, wherein the first unique identifier is assigned at approximately the same time the data object is generated.

3. The method of claim 1, further comprising the step of storing the data object in a memory.

4. The method of claim 3, further comprising the steps of:
  machine reading the machine readable graphical representation of the first unique identifier integrated into one of the hard copies; and
  retrieving the data object from the memory based on the read first unique identifier.

5. The method of claim 1, further comprising the step of electronically transmitting the data object to a remote location.

6. The method of claim 1, further comprising the steps of:
  generating a second data object; and
  selecting portions of the first data object and the second data object to create a third data object comprising at least one of the selected portions.

7. The method of claim 1, further comprising the steps of:
  generating a second data object; and
  assigning a second unique identifier to the second data object, wherein the first and second unique identifiers are related to facilitate correlation of the first and second data objects.

8. The method of claim 7, further comprising the step of assigning a third unique identifier to a group of data objects including the first data object and the second data object.

9. The method of claim 1, wherein the hard copy of the data is comprised of film.

10. The method of claim 1, wherein the hard copy of the data is comprised of reflective paper.

11. The method of claim 1, wherein the first unique identifier is assigned based at least in part on information relating to the data object.

12. The method of claim 1, wherein the multimedia medical data includes analog information, and further comprising the step of digitizing the analog information.

13. The method of claim 1, further including the steps of:
  storing the data object in a memory at an address;
  providing a directory containing the first unique identifier; and
  linking the first unique identifier in the directory with the memory address of the data object.

14. The method of claim 13 further including the step of retrieving the data object from the corresponding address in the memory, and wherein the step of integrating the machine readable graphical representation includes the steps of:
  generating the machine readable graphical representation of the first unique identifier;
  modifying the data object by merging the machine readable graphical representation of the first unique identifier into a portion of the data object corresponding to a viewable portion of the hard copy; and
  outputting the modified data object to a hard copy generator.

15. The method of claim 14, further including the step of storing the modified data object into the memory at the corresponding address.

16. The method of claim 1, wherein the machine readable graphical representation of the first unique identifier includes a gray scale component.

17. A method of managing multimedia medical data, wherein the data are visually presentable in hard copy form, comprising the steps of:
  generating a data object including textual and pixel data components representative of the medical data;
  assigning a first unique identifier to the pixel data component;
  assigning a second unique identifier to the textual data component, wherein the second unique identifier is related to the first unique identifier to facilitate correlation of the textual data component to the pixel data component.

18. A method of managing multimedia medical data, wherein the data are visually presentable in hard copy form, comprising the steps of:
  generating a data object representative of the medical data;
  assigning a first unique identifier to the data object;
  integrating a machine readable graphical representation of the first unique identifier into substantially all hard copies of the corresponding medical data represented by the data object;
  scanning a hard copy of medical information;
  creating a second data object based on the information; and
  assigning a second unique identifier to the second data object based on the information.

19. A method of managing visually presentable multimedia information, comprising the steps of:
  generating a data object representative of the information;
  assigning a first unique identifier to the data object;
  electronically storing the data object in a memory;
  generating a hard copy of the information based on the data object;
  incorporating a machine readable representation of the unique identifier into the hard copy;
  machine reading the representation of the first unique identifier; and
  identifying the data object in the memory corresponding to the information based on the read first unique identifier.

20. The method of claim 19, wherein the unique identifier is assigned at approximately the same time the data object is generated.

21. The method of claim 19, further comprising the step of retrieving the data object from the memory based on the read first unique identifier.

22. The method of claim 19, further comprising the steps of:
  generating a second data object representative of a second information, wherein the first information is related to the second information;
  assigning a second unique identifier to the second data object, wherein the second unique identifier is related to the first unique identifier for correlation of the first and second data objects; and
  storing the second data object in the memory.

23. The method of claim 19, further comprising the step of electronically transmitting the data object to a remote location.

24. The method of claim 19, further comprising the steps of:
  generating a second data object; and
  selecting portions of the first data object and the second data object to create a third data object comprising at least one of the selected portions.

25. The method of claim 19, further comprising the steps of:
  generating a second data object; and
  assigning a second unique identifier to the second data object, wherein the first and second unique identifiers are related to facilitate correlation of the first and second data objects.

26. The method of claim 25, further comprising the step of assigning a third unique identifier to a group of data objects including the first data object and the second data object.

27. The method of claim 19, wherein the hard copy of the data is comprised of film.

28. The method of claim 19, wherein the hard copy of the data is comprised of reflective paper.

29. The method of claim 19, wherein the first unique identifier is assigned based at least in part on information relating to the data object.

30. The method of claim 19, wherein the information includes analog information, and wherein the generating step further comprises digitizing the analog information.

31. The method of claim 19, wherein the step of integrating the graphical representation includes the steps of:

providing a directory containing the first unique identifier; and linking the first unique identifier in the directory with the location of the data object in the memory.

32. The method of claim 19, wherein the machine readable representation of the first unique identifier includes a gray scale component.

33. A method of managing visually presentable multimedia information, comprising the steps of:

generating a data object including textual and pixel components representative of the information;

assigning a first unique identifier to the pixel component;

assigning a second unique identifier to the textual component, wherein the second unique identifier is related to the first unique identifier to facilitate correlation of the textual component to the pixel component;

electronically storing the data object in a memory;

generating a hard copy of the information based on the data object;

incorporating a machine readable representation of one of the first and second unique identifiers into the hard copy;

machine reading the representation of the one unique identifier; and identifying the data object in the memory corresponding to the information based on the read one unique identifier.

34. A method of managing visually presentable multimedia information, comprising the steps of:

generating a data object representative of the information;

assigning a unique identifier to the data object;

electronically storing the data object in a memory;

generating a hard copy of the information based on the data object;

incorporating a machine readable representation of the unique identifier into the hard copy;

machine reading the representation of the unique identifier; and identifying the data object in the memory corresponding to the information based on the read unique identifier;

scanning a hard copy of a second information;

creating a second data object based on the second information; and assigning a second unique identifier to the second data object based on the second information.

35. A management system for multimedia information comprising:

a plurality of information generating devices generating data objects in a plurality of formats;

a converter connected to at least one of the information generating devices for converting information into a format compatible with the formats of data objects generated by other information generating devices;

an indexer for assigning a unique identifier to each data object generated by the information generating devices; and a hard copy generator for generating a hard copy of the information based on at least one of the data objects, wherein the hard copy generator automatically integrates a machine readable representation of the corresponding unique identifier into the hard copy.

36. The management system of claim 35, wherein the indexer assigns the unique identifier at approximately the same time the corresponding data object is generated.

37. The management system of claim 35, further comprising a memory for storing the data objects.

38. The management system of claim 37, further comprising a detector for reading the machine readable representation of the unique identifier integrated into the hard copy, wherein the memory provides the data object in response to the read unique identifier.

39. The management system of claim 35, wherein:

the converter generates a second data object related to the first data object; and the indexer assigns a second unique identifier to the second data object, wherein the second unique identifier is related to the first unique identifier for correlation of the first and second data objects.

40. The management system of claim 35, further comprising a communications link for electronically transmitting the data object to a remote location.

41. The management system of claim 35, wherein the converter generates a second data object, and the management system further comprises an editor for selecting portions of the first data object and the second data object to create a third data object comprising at least one of the selected portions.

42. The management system of claim 35, wherein the indexer assigns a third unique identifier to a group of data objects including the first data object and the second data object.

43. The management system of claim 35, wherein the hard copy of the information is comprised of film.

44. The management system of claim 35, wherein the hard copy of the information is comprised of reflective paper.

45. The management system of claim 35, further comprising:

a scanner for scanning a hard copy of a second information and creating a second data object based on the second information; and wherein the indexer assigns a second unique identifier to the second data object based on the second information.

46. The management system of claim 45, further comprising a second converter connected to the scanner for converting data from the scanner into a format compatible with the formats of data objects generated by other information generating devices.

47. The management system of claim 35, wherein the unique identifier is assigned based on information relating to the data object to uniquely identify the data object.

48. The management system of claim 35, wherein the information includes analog information, and further comprising a digitizer for digitizing the analog information.

49. The management system of claim 35, further comprising:
a memory for storing the data object at an address; and
a directory for storing the unique identifier, wherein the directory links the unique identifier in the directory with the memory address of the data object.

50. The management system of claim 35, wherein the machine readable representation of the unique identifier includes a gray scale component.

51. The management system of claim 35, wherein the multimedia information is in an electronic format corresponding to pixels.

52. The management system of claim 51 wherein the multimedia information is further in a hardcopy film format.

53. The management system of claim 51 wherein the multimedia information is further in a hardcopy paper format.

54. The management system of claim 51 wherein the multimedia information is further in an electronic format corresponding to ASCII text data.

55. The management system of claim 51 wherein the multimedia information is further in an analog video data format.

56. A management system for multimedia information comprising:
a plurality of information generating devices generating data objects in a plurality of formats;
a converter connected to at least one of the information generating devices for converting information into a format compatible with the formats of data objects generated by other information generating devices;
at least one generated data object including textual and pixel data components;
an indexer for assigning a first unique identifier to the pixel data component and a second unique identifier to the textual data component, wherein the second unique identifier is related to the first unique identifier to facilitate correlation of the textual data component to the pixel data component; and
a hard copy generator for generating a hard copy of the information based on at least one of the data objects, wherein the hard copy generator automatically integrates a machine readable representation of the corresponding unique identifier into the hard copy.

57. A database management system for a database of multimedia data objects generated by a plurality of data generating devices, wherein the data objects are visually presentable to a user in hard copy form, comprising:
an indexer associated with each of the data generating devices for assigning a unique identifier to each data object generated by the data generating devices; and
a hard copy generator for generating a hard copy of at least one of the data objects, wherein the hard copy generator includes a machine readable representation of the unique identifier in each hard copy.

58. The management system of claim 57, wherein each indexer assigns the unique identifier at approximately the same time the corresponding data object is generated.

59. The management system of claim 58, wherein at least one of the indexers includes a converter for converting data objects generated by the corresponding data generating device into a format compatible with each of the other data objects.

60. The management system of claim 57, further comprising a memory for storing the data objects.

61. The management system of claim 60, further comprising a detector for reading the representation of the unique identifier integrated into the hard copy, and wherein the memory provides the data object in response to the read unique identifier.

62. The management system of claim 57, wherein:
at least one of the data generating devices generates a first data object and the corresponding indexer assigns a first unique identifier to the first data object;
at least one of the data generating devices generates a second data object and the corresponding indexer assigns a second unique identifier to the second data object; and
the second unique identifier is related to the first unique identifier for correlation of the first and second data objects.

63. The management system of claim 57, further comprising a communications link for electronically transmitting data objects to a remote location.

64. The management system of claim 57, wherein at least one of the data generating devices generates a second data object, and the management system further comprises an editor for selecting portions of the first data object and the second data object to create a third data object comprising at least one of the selected portions.

65. The management system of claim 64, wherein at least one of the indexers assigns a third unique identifier to a group of data objects including the first data object and the second data object.

66. The management system of claim 57, wherein the hard copy of the data object is comprised of film.

67. The management system of claim 57, wherein the hard copy of the data object is comprised of reflective paper.

68. The management system of claim 57, further comprising:
a scanner for scanning a hard copy of information and creating a second data object based on the information; and
wherein the indexer corresponding to the second data object assigns a second unique identifier to the second data object based at least in part on the hard copy.

69. The management system of claim 68, further comprising a converter connected to the scanner for converting data from the scanner into a format compatible with the formats of data objects generated by other data generating devices.

70. The management system of claim 57, wherein the identifier is assigned based at least in part on information relating to the data object.

71. The management system of claim 57, wherein the data object includes analog data, and further comprising a digitizer for digitizing the analog data.

72. The management system of claim 57, further comprising:
a memory for storing each data object at an address; and
a directory for storing each unique identifier, wherein the directory links the unique identifier in the directory with the memory address of the corresponding data object.

73. The management system of claim 57, wherein the machine readable representation of the unique identifier includes a gray scale component.

74. A database management system for a database of multimedia data objects generated by a plurality of data generating devices, at least one of the data objects including textual and pixel data components, wherein the data objects are visually presentable to a user in hard copy form, comprising:

an indexer associated with each of the data generating devices for assigning a unique identifier to each data object generated by the data generating devices;

a hard copy generator for generating a hard copy of at least one of the data objects, wherein the hard copy generator includes a machine readable representation of the unique identifier in each hard copy;

the indexer corresponding to a data object including textual and pixel data components assigning a first unique identifier to the pixel data component and assigns a second unique identifier to the textual data component, wherein the second unique identifier is related to the first unique identifier to facilitate correlation of the textual data component to the pixel data component.

* * * * *